(12) United States Patent
Ning

(10) Patent No.: US 6,477,221 B1
(45) Date of Patent: Nov. 5, 2002

(54) SYSTEM AND METHOD FOR FAST PARALLEL CONE-BEAM RECONSTRUCTION USING ONE OR MORE MICROPROCESSORS

(75) Inventor: Ruola Ning, Fairport, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/784,331

(22) Filed: Feb. 16, 2001

(51) Int. Cl.$^7$ .................................................. A61B 6/03
(52) U.S. Cl. ................................................ 378/4; 378/901
(58) Field of Search ............................. 378/4, 15, 901

(56) References Cited

U.S. PATENT DOCUMENTS

| | | | |
|---|---|---|---|
| 5,170,439 A | | 12/1992 | Zeng et al. |
| 5,253,171 A | * | 10/1993 | Hsiao et al. .................. 378/10 |
| 5,257,183 A | | 10/1993 | Tam |
| 5,278,884 A | | 1/1994 | Eberhard et al. ............... 378/4 |
| 5,333,164 A | * | 7/1994 | Tam ............................. 378/14 |
| 5,365,560 A | | 11/1994 | Tam ............................. 378/8 |
| 5,390,226 A | | 2/1995 | Tam ............................. 378/19 |
| 5,400,255 A | | 3/1995 | Hu |
| 5,461,650 A | | 10/1995 | Tam ............................. 378/4 |
| 5,517,602 A | | 5/1996 | Natarajan |
| 5,671,265 A | | 9/1997 | Andress .................... 378/98.11 |
| 5,802,133 A | | 9/1998 | Kawai et al. ................... 378/4 |

OTHER PUBLICATIONS

P. Grangeat, "Mathematical Framework Of Cone Beam 3D Reconstruction Via The First Derivative Of the Radon Transform", Mathematical Methods in Tomography, Herman, Lewis, Natterer (eds) Lecture Notes in Mathematics, No. 1497, pp. 66–97, Spring Verlag (1990).

L.A. Feldkamp et al., "Practical cone–beam algorithm", J. Opt. Soc. Am. A/vol. 1, No. 6, Jun. 1984, pp. 612–619.

Y. Weng et al., "A Reconstruction Algorithm for Helical Cone–Beam SPECT", IEEE Transactions on Nuclear Science, vol. 40, No. 4, Aug. 1993, pp. 1092–1101.

B. Smith, "Cone–beam tomography: recent advances and a tutorial review", Optical Engineering, vol. 29, No. 5, May 1990, pp. 524–534.

H. Tuy, "An Inversion Formula For Cone–Beam Reconstruction", SIAM J. Appl. Math, vol. 43, No. 3, Jun. 1983, pp. 546–552.

B.D. Smith, "Image Reconstruction from Cone–Beam Projections:Necessary and Sufficient Conditions and Reconstruction Methods", IEEE Transactions on Medical Imaging, vol. M1–4, No. 1, Mar. 1985, pp. 14–15.

* cited by examiner

*Primary Examiner*—David V. Bruce
(74) *Attorney, Agent, or Firm*—Blank Rome Comisky & McCauley LLP

(57) ABSTRACT

Cone-beam reconstruction is performed within a practically acceptable time on a computer having one or more microprocessors. The calculations involved in the reconstruction are divided into calculations to be performed on the MMX, ALU and SSE units of each of the microprocessors. For pure floating-point data, it is preferred to use the MMX unit to adjust the data address and map data and to use the SSE unit to perform the backprojection. The data are partitioned by z-line so that the data to be processed in each stage of the backprojection fit within the L1 cache.

33 Claims, 4 Drawing Sheets

SYSTEM AND METHOD FOR FAST PARALLEL CONE-BEAM RECONSTRUCTION USING ONE OR MORE MICROPROCESSORS

STATEMENT OF GOVERNMENT INTEREST

The present invention was supported in part by NIH Grants 2R01HL48603-05 and 1R41HL59703. The government has certain rights in this present invention.

FIELD OF THE INVENTION

The present invention is directed to a system and method for cone-beam reconstruction in medical imaging or the like and more particularly to such a system and method implemented on one or more microprocessors. The present invention is also useful for nondestructive testing, single photon emission tomography and CT-based explosive detection, micro CT or micro cone beam volume CT, etc.

DESCRIPTION OF RELATED ART

Cone-beam reconstruction has attracted much attention in the medical imaging community. Examples of cone-beam reconstruction are found in the commonly assigned U.S. Pat. Nos. 5,999,587 and 6,075,836 and U.S. patent application Ser. Nos. 09/589,115 and 09/640,713, whose disclosures are hereby incorporated by reference in their entireties into the present disclosure.

CT (computed tomography) image reconstruction algorithm can be classified into two major classes: filtered backprojection (FBP) and iterative reconstruction (IR). The filtered backprojection is more often discussed because it is accurate and amenable to fast implementation. The filtered backprojection can be implemented as an exact reconstruction method or as an approximate reconstruction method, both based on the Radon transform and/or the Fourier transform.

The cone beam reconstruction process is time-consuming and needs a lot of computing operation. Currently, the cone beam reconstruction process is prohibitively long for clinical and other practical applications. Considering a set of data with projection size N=512, since the time and computation for FBP is $O(N^4)$, the reconstruction need GFLOPS (gigaflops) of computation. Usually, the use of an improved algorithm and a faster computing engine can achieve fast cone beam reconstruction.

Existing fast algorithms for reconstruction are based on either the Fourier Slice Theorem or a multi-resolution re-sampling of the backprojection. Algorithms based on the Fourier Slice Theorem use interpolations to transform the Fourier projection data from the polar to the Cartesian grid, from which the reconstruction can be obtained by an inverse FFT. Many works have been done to bring down the FBP time, and most of them are focused on fan-beam data. These include the linogram method and the "links" method as well as related fast methods for re-projection. An approximate method has been proposed based on the sinogram and "link"; such a method works for 2D FBP and can achieve $O(N^2 \log N)$ complexity. The "link" method has been extended to 3D cone-beam FBP; after rebinning the projection data in each row, the same method as in 2D can be applied to rebinning data, and data processing time can be brought down to $O(N^3 \log N)$ complexity for cone beam reconstruction. Another fast algorithm has been presented, using Fast Hierarchical Backprojection (FHBP) algorithms for 2D FBP, which address some of the shortcomings of existing fast algorithms. FHBP algorithms are based on a hierarchical decomposition of the Radon transform and need $O(N^2 \log N)$ computing complexity for reconstruction. Unfortunately, experimental evidence indicates that for reasonable image sizes, $N \approx 10^3$, the realized performance gain over the more straightforward FBP is much less than the potential N/logN speedup. A loss in reconstruction quality comes as well when compared with the Feldkamp algorithm. In real implementation, the total reconstruction time depends not only on the computing complexity, but also on the loop unit time. The 3D cone beam FBP mentioned above which uses the link method needs additional memory space to store the "link" area. The link reconstruction table area containing interpolation coefficients and address information to access "link" data takes $O(N^3)$ additional memory and lowers the performance because the memory access time. The speed-up is smaller than N/logN.

A customized backprojection hardware engine having parallelism and pipelining of various kinds can push the execution speed to the very limit. The hardware can be an FPGA based module or an ASIC module, a customized mask-programmable gate array, a cell-based IC and field programmable logic device or an add-in board with high speed RISC or DSP processors. Those boards usually use high-speed multi-port buffer memory or a DMA controller to increase data exchanging speed between boards. Some techniques, like vector computing and pre-interpolating projection data, are used with the customized engine to decrease reconstruction operation. Most of the customized hardware is built for 2D FBP reconstruction applications. No reconstruction engine-based a single or multiple microprocessors that is specially designed for fast cone beam reconstruction is commercially available.

A multi-processor computer or a multi-computer system can be used to accelerate the cone beam reconstruction algorithm. Many large-scale parallel computers have tightly coupled processors interconnected by high-speed data paths. The multi-processor computer can be a shared memory computer or a distributed memory computer. Much work has been done on the large-scale and extremely expensive parallel computer. Most of that work uses an algorithm based on the 3D Radon transform. As an example, the Feldkamp algorithm and two iterative algorithms, 3D ART and SIRT, have been implemented on large-scale computers such as Cray-3D, Paragon and SP1. In such implementations, the local data partition is used for the Feldkamp algorithm and the SIRT algorithm, while the global data partition is used for the ART algorithm. The implementation is voxel driven. The communication speed between processors is important to the reconstruction time, and the Feldkamp implementation can gain best performance in Multiple Instruction Multiple Data (MIMD) computers. Parallel 2D FBP has been implemented on Intel Paragon and CM5 computers. Using customized accelerating hardware or a large-scale parallel computer is not a cost-effective fast reconstruction solution, and it is not convenient to modify or add a new algorithm for research work.

In a distributed computing environment, many computers can be connected together to work as a multi-computer system. The computing tasks are distributed to each computer. Usually the parallel program running on a multi-computer system uses some standard library such as MPI (message passing interface) or PVM (parallel virtual machine). Parallel reconstruction has been tested on a group of Sun Sparc2 computers connected with an Ethernet network, and the implementation is based on the PVM library. The Feldkamp algorithm has been implemented on heterogeneous workstation clusters based on the MPI library. The implementation runs on six computer clusters, and the result shows that the implementation in load balancing resulted in processor utilization of 81.8%, and use of asynchrous communication has improved processor utilization to 91.9%. The biggest disadvantage of multi-computer clusters is that communication speed decreases reconstruction speed. Since cone beam reconstruction involves a large data memory, the data is usually distributed into each computer. The computers need to exchange data in the backprojection phase. The memory communication is a big trade-off for reconstruction speed. Another disadvantage is the inability to get a small size reconstruction engine with multi-computer clusters. There are also some attempts to implement cone beam reconstruction on distributed computing technology such as COBRA (common object request broker architecture and specification). Usually the distributed computing library costs more communication time trade-off than directly using the MPI library, thus resulting in lower reconstruction speed.

Besides parallelism between processors, a single processor can gain data and operation parallelism with some micro-architecture techniques. Instruction-level Parallelism (ILP) is a family of processor and compiler design techniques that speed up execution by causing individual machine operations to execute in parallel. Modern processors can divide instruction executing into several stages; some techniques such as pipeline and branch prediction permit the execution of multiple instructions simultaneously. To enable data processing parallelism, some processors add single instruction multiple data (SIMD) instructions, which can process several data in one instruction. Such processors include Intel's IA-32 architecture with MMX™ and SSE/SSE2, Motorola's PowerPC™ with AltVeC™ and AMD Athlon with 3Dnow™. However, to date, such parallelism has not been exploited in cone-beam reconstruction.

SUMMARY OF THE INVENTION

In light of the above, it will be readily apparent that a need exists in the art to perform cone-beam reconstruction at a practically acceptable speed without the need for customized hardware or a large-scale computer. It is therefore an object of the invention to provide a system and method for cone-beam reconstruction which can be performed quickly on inexpensive, widely available equipment.

To achieve the above and other objects, the present invention is directed to a practical implementation for high-speed CBR on a commercially available PC based on hybrid computing (HC). Feldkamp CBR is implemented with multi-level acceleration, performing HC utilizing single instruction multiple data (SIMD) and making execution units (EU) in the processor work effectively. The multi-thread and fiber support in the operating system can be exploited, which automatically enable the reconstruction parallelism in a multi-processor environment and also make data I/O to the hard disk more effective. Memory and cache access are optimized by proper data partitioning. Tested on an Intel Pentium III 500 Mhz computer and compared to the traditional implementation, the present invention can decrease filtering time by more than 75% for 288 projections each having $512^2$ data points and can save more than 60% of the reconstruction time for $512^3$ cube, while maintaining good precision with less than 0.08% average error. The resulting system is cost-effective and high-speed. An effective reconstruction engine can be built with a commercially available Symmetric Multi-processor (SMP) computer, which is easy and inexpensive to upgrade along with newer PC processors and memory with higher access speed.

In the present invention, the Feldkamp algorithm cone beam reconstruction (FACBR) can achieve high speed with good precision. The test environment is an Intel Pentium III 500 Mhz with 640 MB 100 Mhz memory. The result shows that the reconstruction for a $512^3$ cube with 288 projections can be finished in less than 20 minutes and maintains good precision, while the old implementation required more than 100 minutes. Several simulated phantoms have been used to test the precision of the HC FACBR. Comparing the reconstructed image with a simulated phantom image and images reconstructed by the traditional method shows less than a 0.04% average error compared to traditional method images and good precision to computer-simulated phantoms. A linear attenuation coefficient distribution of a three-dimensional object can be reconstructed quickly and accurately.

A higher speed SSE-2 enabled Pentium IV and a 2- or 4-processor PC are expected to permit $512^3$ cube FACBR in a few minutes in the future. FACBR is implemented with multi-level acceleration and hybrid computing utilizing the SIMD and ILP technology. The memory and cache access are optimized by proper data partition. Compared to implementation on a large-scale computer and computer clusters, the present invention is cost-effective and high-speed. A market available SMP computer provides an effective reconstruction engine which is easy and inexpensive to be upgraded along with newer PC processors. By contrast, custom built hardware is expensive and very difficult to upgrade.

A high-speed implementation will be disclosed for FACBR on a PC. Techniques for hybrid execution (HE) and hybrid data (HD) will also be disclosed. With these hybrid computing features, good memory organization and instruction optimization, a high speed Feldkamp implementation can be implemented on a general purpose PC with a high performance to price ratio. The HD and HE can also be applied to implementation on other hardware platforms to improve the FACBR performance. With higher clock frequency processors and an inexpensive market available SMP PC, it is possible to gain good performance as done by expensive, inconvenient customized hardware. As a commercial market available PC is used to achieve high performance, it is convenient to design new algorithms and a new system for cone beam reconstruction, and it is useful to integrate an image grab system and 3D rendering system, in a single system which is easy to configure and upgrade.

As Intel x86 CPU frequency has increased to the GHz level, it is practical and economically feasible to build a Multi-Processor x86-based high-speed cone beam reconstruction computing engine. Although the Feldkamp algorithm is an approximate cone beam reconstruction algorithm, it is a practical and efficient 3D reconstruction algorithm and is a basic component in a few exact cone-beam reconstruction algorithms including the present invention.

The present invention implements parallel processing on a single microprocessor or multiple processors. The use of hybrid computing (both fixed and floating point calculation) accelerates the cone-beam reconstruction without reducing the accuracy of the reconstruction and without increasing image noise. Those characteristics are particularly important for the reconstruction of soft tissue, e.g., cancer detection.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

A preferred embodiment of the present invention will now be set forth in detail with reference to the drawings.

Figure 1:
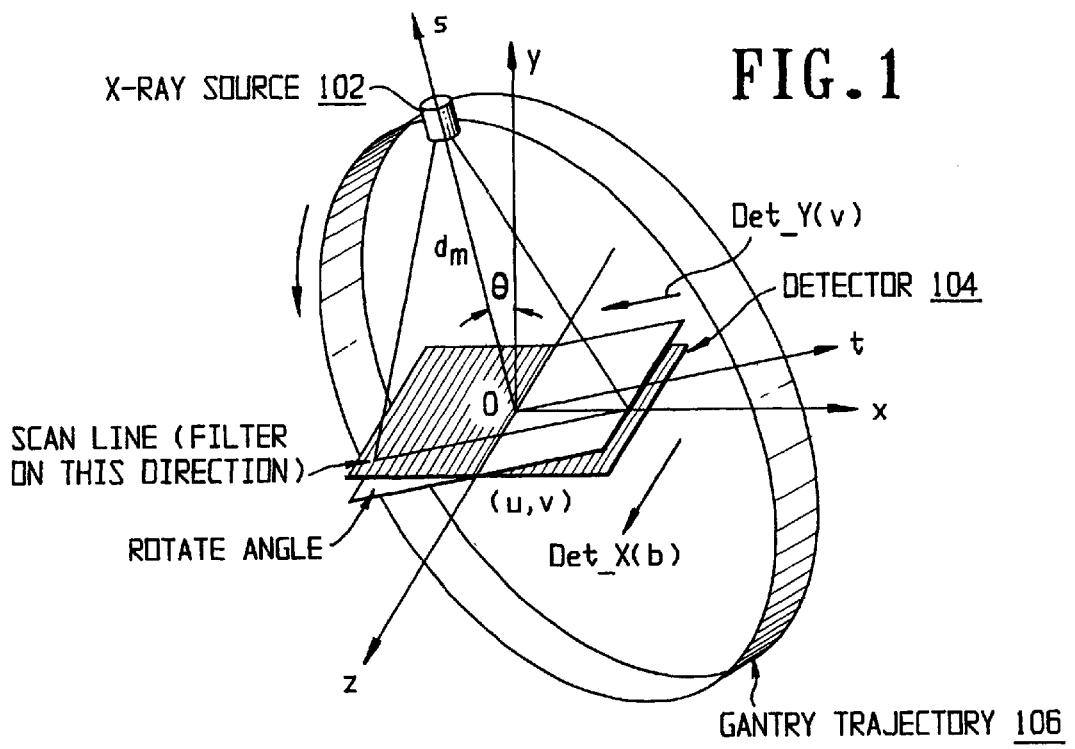
FIG. 1 shows a cone-beam coordinate system used in reconstruction in the preferred embodiment.

The preferred embodiment will be disclosed in terms of the coordinate system shown in FIG. 1. The O-XYZ is the world coordinate system. The X-Y-Z axis gives the physical coordinates for the reconstructed voxels. The Z-axis is the rotation axis. The t-s axis is the rotated gantry X-Y coordinate system. The s-axis always passes through the x-ray source and is perpendicular to the detector plane.

Several groups have investigated the reconstruction for the cone beam geometry. The most efficient algorithm in use is the one developed by Feldkamp, L. A., Davis, L. C., and Kress, J. W., "Practical Cone-Beam Algorithm," *J. Opt. Soc. Am. A* 1: (6) 612–619 (1984), and Kak, A. C., and Slaney, M., Principles of Computerized Tomographic Imaging, IEEE Press, 1988. In this algorithm, the projection data is backprojected onto an image buffer with each detected ray backprojected in its direction. Pixels in the image buffer are incremented by the amount of the projection pixel. The projection must be filtered prior to backprojection.

The coordinates used in the discussion are shown in FIG. 1 and are defined relative to an x-ray source 102, a detector 104 and a gantry 106. It is assumed that the projection of the object $P(\theta)$ at angle $\theta$ is indexed by detector coordinates u and v. The reconstructed voxel values are indexed by physical coordinates x, y, and z. The center of rotation is the z-axis. The distance from the x-ray focal spot to the rotation axis is $d_{so}$. By scaling the projection pixel sizes, the vertical axis of the detector can be moved to the z-axis. By subsequently scaling the geometry, the pixel sizes at the z-axis can be made one. These scaling simplify the computations in the reconstruction algorithm. The Feldkamp algorithm falls into the class of filtered backprojection algorithms. The implementation of the Feldkamp algorithm contains following steps: a) Apply weight and ramp filter to the projections data; this is done by applying a weight to each $P(\theta)$ value and applying convolution to data in rows or in columns with filter data.

$$P_\theta^{filter}(i,j) = \left(\frac{d_{so}}{\sqrt{d_{so}^2 + i^2 + j^2}} P_0(i,j)\right) * h(i) \quad (1)$$

b) Backproject the data $P_\theta^{filter}$ (u,v) to the reconstructed voxel f (x,y,z):

$$f(x,y,z) = \int_0^{2\pi} u^2 P_\theta^{filter}(u \cdot t, u \cdot z) d\theta \quad (2)$$

$$u = \frac{d_{so}l}{d_{so}-s}$$

$$t = x \cdot \cos\theta + y \cdot \sin\theta$$

$$s = y \cdot \cos\theta - x \cdot \sin\theta$$

As noted above, (t,s) is the coordinate in gantry system, which is the rotation transform of the X-Y axis with angle $\theta$.

Let the reconstruction volume be $N_x \times N_y \times N_z$ voxels in the x, y, and z directions. For M projections, let $\theta$ be the angle difference between consecutive angle position and $P\theta(i, i)$ is $N_i \times N_j$ pixels. The complexity of the problem is roughly linear with the total number of voxels and linear with the number of projection view angles. Doubling the number of voxels roughly doubles the processing time. Doubling the dimension in each direction produces an eight-fold increase in the required processing. Doubling the number of views doubles the processing. As the number of voxels increases, the number of angular views must also increase to maintain the same peripheral resolution. This is an important factor in reconstructing larger objects or reconstructing with better resolution. For the case in which the image size is N×N, the number of projections M usually should be the same level as N, and thus the complexity of the problem is $O(N^4)$. The majority of the computation is in the backprojection.

Figure 2:
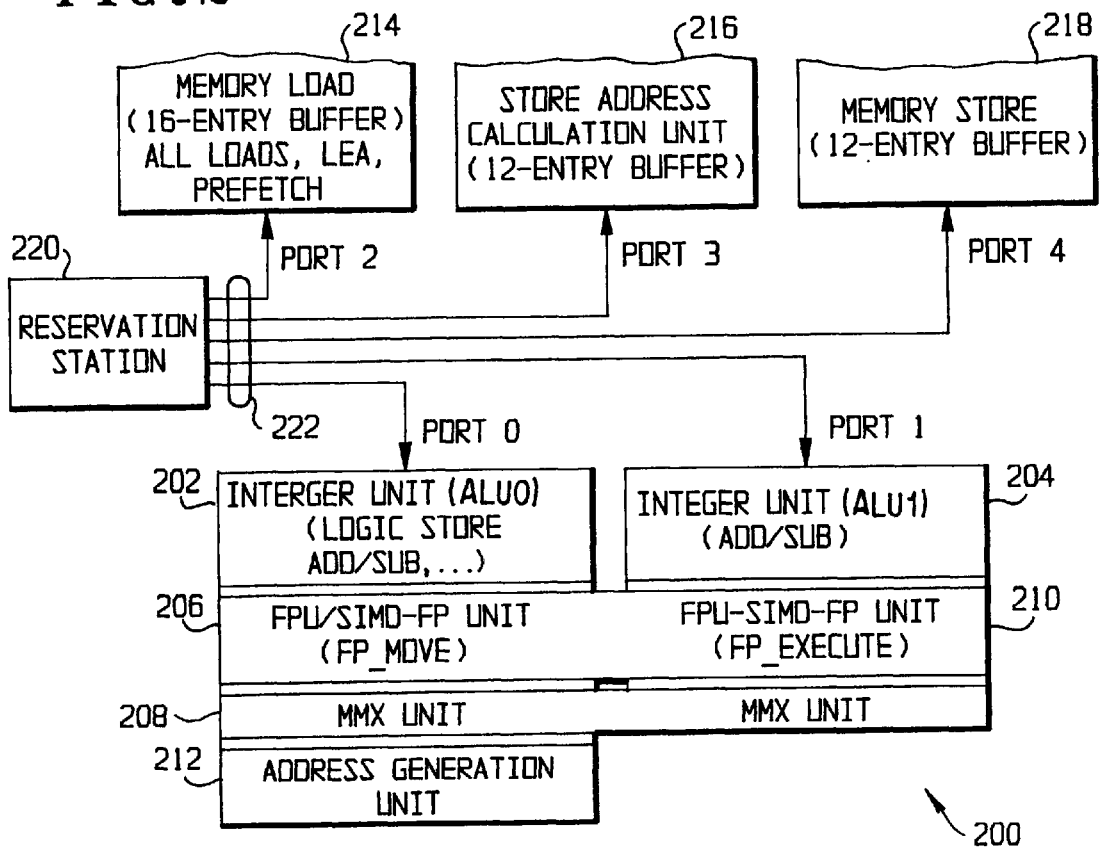
FIG. 2 shows the architecture of an Intel x86 processor.

The Intel x86 architecture diagram is shown in FIG. 2. The Intel processor 200 has multiple execution units (EU's) to do integer and float operations simultaneously. In an Intel Pentium III, there are two integer unit (ALU0 202 and ALU1 204), one float unit (FPU) 206, one MMX unit 208 to process 8-bit and 16-bit integers in parallel, and one Streaming SIMD Executing unit (SSE) to process four 32-bit single-precision float point data in parallel 210. Also present are an address generation unit 212, a memory load 214, a store address calculation unit 216, a memory store 218 and a reservation station 220. The SIMD instruction in the SSE enables four float integer operations at one instruction. The Pentium III processor has five pipelines 222 to exploit the parallelism in instruction execution. In each clock cycle, the processor core may dispatch zero or one μop on a port to any of the five pipelines for a maximum issue bandwidth of five μops per cycle. Each pipeline connects to different EUs. For all different versions of the C/C++ compiler for Intel processor, the normal C/C++ code will only be able generate code to utilize the integer unit ALU and float unit FPU. To use the hardware resource of the MMX unit and the SSE unit, either special intrinsic or manually written assembler code is used. There are two levels of cache in Pentium III processor. Level one (L1) cache is the on-chip cache subsystem and consists of two 16-Kbyte four-way set associative caches with a cache line length of 32 bytes for instruction and data. The data cache has eight banks interleaved on four-byte boundaries. Level two (L2) cache is off-chip but in the same processor package. It usually has a size from 128 Kbytes to 1 Mbyte. L2 usually has a latency from 4 to 10 cycles for data access. When the processor needs to fetch instructions or data, L1 is much faster than L2, and L2 is faster than access to main memory.

It is possible to construct a multi-processor computer with several processors; most such of computers now on the market are SMP with two or four processors. Usually the operating system running on the computer has some techniques such as multi-thread and multi-process to utilize the multi-processor's hardware resource. For example, Microsoft Windows has Win32 threads, and Unix/Linux has pthread support. It is contemplated that the preferred embodiment will most often be implemented with Windows NT/2000, which has multi-thread and fiber support, which automatically reconstructs parallelism in a multi-processor environment.

Several tricks can be used to minimize the actual number of operations in the backprojection loop, e.g. by changing the order in which x, y and z are incremented; applying a special boundary to reconstruction voxels; pre-interpolating projection data to allow for the simplest possible interpolation in the actual inner loop. The basic performance for a single-processor computer system can be expressed in terms of $$T=n*CPI*t \quad (3)$$

where T is the total time to execute, n is the number of instructions executed, t is the time per instruction, and CPI is the number of cycles per instruction. Decreasing the clock time t is a matter of engineering. Generally, smaller, faster circuits lead to better clock speed.

Decreasing the other two factors involves some version of parallelism. There are several levels of parallelism: First, a single program can be broken into constituent parts, and different processors compute each part; this is called Program-Level Parallelism. Second, some techniques such as pipelining allow more throughputs by the execution of overlapping instructions; this is called Instruction-Level Parallelism. Finally, Low-level parallelism is primarily of interest to designers of the arithmetic logic units and relatively invisible to user; this is called Arithmetic and Bit-Level Parallelism. The preferred embodiment relies primarily on Program-Level Parallelism and Instruction-Level Parallelism. The program level parallelism is manifested in independent sections of a program or in individual iterations of a loop. Such parallelism may be exploited by employing multiple processors. The Instruction-Level Parallelism has two basic kinds: Individual instructions are overlapped (executed at the same time) in the processor, a given instruction is decomposed into sub operations and the sub operations are overlapped.

As described in Feldkamp algorithm, a set of M projections is used, each projection having a size NxN pixels, to reconstruct an $N^3$ cube. Each projection requires $N^3$ loop calculations to do backprojection. M projections require $M*N^3$ loop calculations. Usually, M should be on the same level as N to get a better result. The total actual reconstruction time can be written as:

$$T_{recon}=k*t_{unit}* O(N^4) \quad (4)$$

If the algorithm is not changed, the $O(N^4)$ computation complexity of the Feldkamp algorithm cannot be decreased. However, since the total time also depends on factor k and loop unit time $t_{unit}$, a smaller factor k and a shorter back project loop unit time $t_{unit}$, will decrease the reconstruction time.

Figure 3:
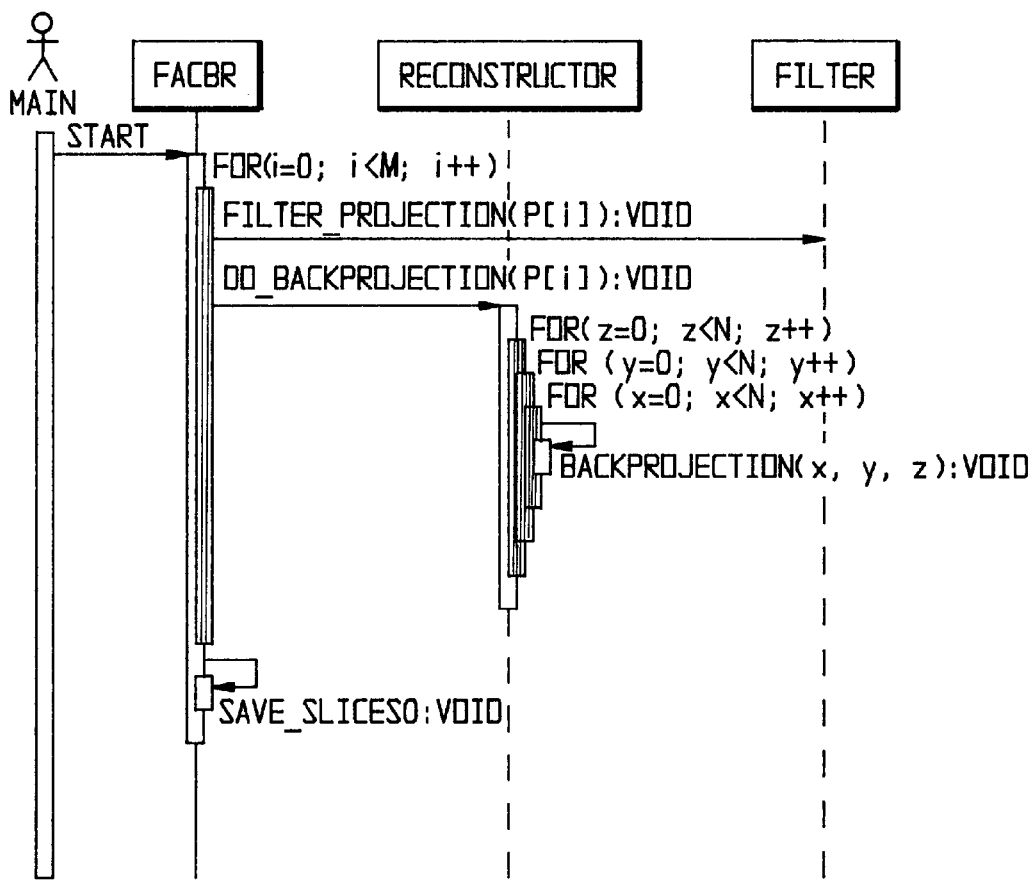
FIG. 3 shows an UML diagram of a known FACBR implementation.

The normal FACBR implementation can explained with a unified modeling language (UML) sequence diagram as FIG. 3. When the FACBR process starts, the M projection data are loaded one by one, each being filtered according to equation (1); then the filtered data are used to backproject to each voxel f(x,y,z). After the backprojection is finished for all data, the reconstruction is finished, and the data are saved or rendered in a 3D display. Usually the filtering time is about 1/15 to 1/30 of the backprojection time or less. In the implementation with C/C++ code according to FIG. 3, only the FPU and to a lesser extent the ALU are used during the FACBR process, and the most powerful EU's are wasted.

It is known in the art that there are four possible forms of parallelism in Feldkamp algorithm implementation: pixel parallelism, projection parallelism, rays parallelism and operation parallelism. In the reconstruction process, all voxels and projections are independent of one another, and rays can be backprojected independently. The operations for filtering and backprojection of each projection are independent; the low level multiplication and addition operation can even be divided independently. To implement fast cone beam reconstruction, the following methods are applied in the FACBR implementation:

a) Split the FDK backprojection procedure into two phases: projection map generation to calculate (u,t,s) and data backprojection to calculate f(x,y,z). Equation (2) shows that (u,t,s) depends only on (x,y), so that the projection map needs only $O(N^3)$ computation time; thus both k and $t_{unit}$ can be decreased.

b) Use some a priori knowledge to generate some boundary as a sphere or cylinder; the computation can be skipped for some voxels which are outside the boundary and unable to be reconstructed, thereby providing a smaller k. If the reconstructed voxels are visualized as a cube with N length, then the full number of voxels is on the order of $N^3$, but with a cylinder boundary, the reduced number of voxels lowers k by $\pi/4$ smaller, and the sphere boundary will make k become $\pi/6$ smaller.

c) The FACBR process involves a large memory requirement; for N=512, the data of one projection or one slice will be 1 Mbyte. This is even bigger than the L2 size. $t_{unit}$ actually takes into account memory access time and computing time for each voxel at (x,y,z). Cache miss during the reconstruction process will decrease the performance, so the data should be arranged in the memory so that most of the data access is near to the processor, that is, the processor obtains more data from L1 than from L2 and more data from L2 than from main memory d) To get shorter $t_{unit}$, the backprojection loop core needs to be optimized. Manually written assembly language can be used to control the EU's to work in parallel, which is Hybrid Execution (HE) to decrease both k and $t_{unit}$. As float point data always take more computing time than fixed point data, part of the intermediate result can be processed in fixed point data, so that Hybrid Data (HD) is used to decrease the $t_{unit}$.

e) The reconstruction data and projection data processing can be split into several parts and run on different processors when SMP is available. With n-processor SMP, when the fraction of the task which cannot be converted to concurrent work is f, the k value is decreased with a theoretic speed-up as n/(1+(n−1)f) according to Amdahl's law. A multi-processor computer works by multithread implementation and carefully allocates the tasks among the processors. Operating systems capable of controlling a multi-processor computer in such a manner are known in the art, as noted above. For a single processor, the context switching will sacrifice the CPU time and so may actually decrease the performance, so it is contemplated that the multi-thread method will be used only when SMP is available.

The method described above has been implemented and tested on an ordinary PC having the specifications set forth in Table 1 below:

TABLE 1

| Machine | CPU Frequency | Physical Memory | SIMD/ILP Support |
|---|---|---|---|
| Pentium III | 500 MHz | 640 MB | MMX, SSE |

Microsoft Visual C++ 6.0 and Intel C++ 4.5 were used as developing tools. In the traditional implementation, a pure float point (PF) calculation was performed and consequently only the FPU was fully used because of the compiler. Intrinsic and fine-tuned assembler code provide a hybrid computing method. Namely, both floating-point and fixed-point computing are used during the reconstruction process with HD, so as to fully utilize the EUs in Pentium III processors.

Parallelism considerations will now be described. The first is the use of hybrid execution (HE) and hybrid data (HD).

Figure 4:
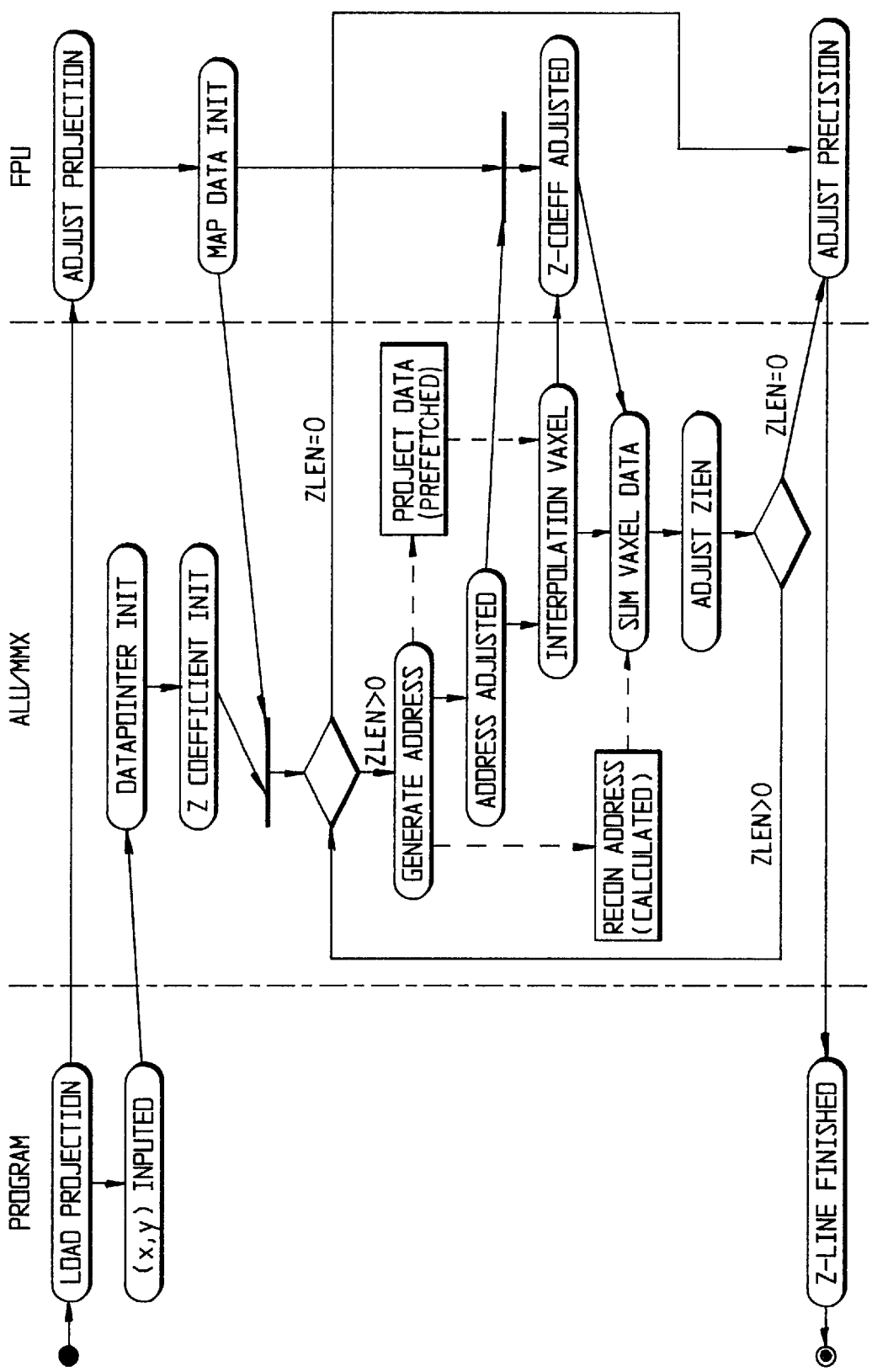
FIG. 4 shows a UML diagram of hybrid execution according to the preferred embodiment.

HD is used to decrease and make ALU units work in parallel. As the SSE unit is independent from the FPU unit and the MMX unit, the SSE unit can work with the ALU unit, the MMX unit and even the FPU unit simultaneously, thus allowing a hybrid execute mode for either PF data or HD. There are different methods to use the EUs to accelerate the FACBR process. The map data and some intermediate results can be processed by the ALU in fixed point data format, and the reconstruction data and finally output results can be processed in floating point format. That hybrid data format for different data and stages can improve the EU's efficiency. For PF data, the best method is to use the MMX unit to adjust the data address and map data, and to use the SSE to do the backprojection calculation. The MMX can process data address and map data for two or more points, while the ALU can deal with only one point. The HE method for PF can be shown as a UML activity diagram in FIG. 4.

Since the MMX unit in a Pentium III processor can only process 8-bit and 16-bit integer multiplication, it is not so effective to do HE for HD data as to do HE for PF data. However, with new processor techniques such as SSE2 in the Pentium IV processor, the hybrid execution with HD will gain more improvements on speed.

Figure 5:
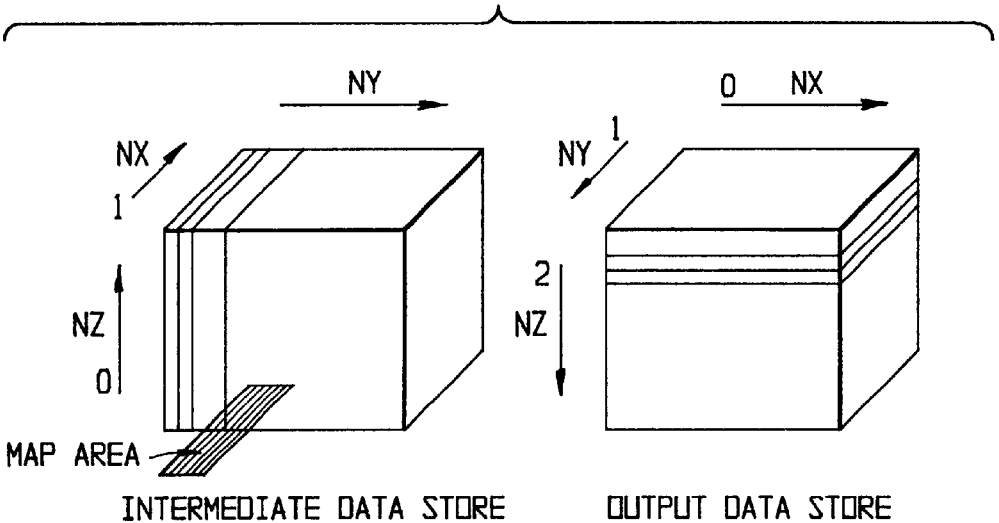
FIG. 5 shows a data partition scheme used in the preferred embodiment.

The second parallelism consideration is the data partition schema. For reconstruction for different axes, the reconstruction data are partitioned into different sub-units. A data partition scheme is shown in FIG. 5. Data are stored in memory as a one-dimensional array, in which the index of each data point increases for z, then for x and last for y. Data are processed in z-lines because the same projection data u value can be used for one z-line In fact, the projection data used to do backprojection for voxels in one z-line are actually in two adjacent u-lines, since four adjacent points (two in each of the adjacent u-lines) are used to interpolate the data for one voxel in the z-line. It is thus easy to prefetch the projection line data and a reconstruction z-line into cache, as one line occupies only 4 N bytes. For N=512, the whole data line only need 6 Kbytes, which is suitable for both L1 and L2 caches. After all voxels are reconstructed, a special in-place 3D transpose operation is done to change the reconstruction data to a one-dimensional array whose index increases from x, then y and last for z. The transpose operation is done in place because the whole $N^3$ cube takes $4 N^3$ bytes of memory. The symmetry along the Z-axis can also be used in reconstruction one Z-line to save the time to calculate the map data.

To ensure precision when improving on cone beam reconstruction speed, first the reconstruction accuracy of the implementation will be determined using computer-simulated phantom. Second, the reconstruction error noise level and uniformity of the reconstructed images are quantified using both pure float point implementation and HD computing implementation, and the reconstruction results from the two implementations are compared with both simulated phantom and experimental phantom data. After it is determined that the HC implementation does not introduce artifacts and unacceptable reconstruction errors, the speedup of MC implementation is evaluated compared to normal pure float-point computing reconstruction. Experimental phantom data are also used to evaluate the effectiveness of the implementation in the real world.

Two simulated phantoms shown in Table 2 below are used to evaluate the precision. The Shepp Logan phantom is used as a general precision error compare reference. The cylinder phantom is used to compare the precision error at different z positions. Normally, the Feldkamp Algorithm has the best result at center slice, and the precision error increases for the slices at two ends. The cylinder phantom is used to check whether the HD and PF precision error varies with z-distance to center.

TABLE 2

| a | b | c | $x_0$ | $y_0$ | $z_0$ | $\alpha$ | $\beta$ | $\mu$ |
|---|---|---|---|---|---|---|---|---|
| Shepp Logan Phantom with 11 Ellipse | | | | | | | | |
| 0.6900 | 0.920 | 0.900 | 0.000 | 0.000 | 0.000 | 0.0 | 0.00 | 2.00 |
| 0.6624 | 0.874 | 0.880 | 0.000 | 0.000 | 0.000 | 0.0 | 0.00 | −0.98 |
| 0.4100 | 0.160 | 0.210 | −0.22 | 0.000 | −0.25 | −72.0 | 0.00 | −0.02 |
| 0.3100 | 0.110 | 0.220 | 0.220 | 0.000 | −0.25 | 72.0 | 0.00 | −0.02 |
| 0.2100 | 0.250 | 0.500 | 0.000 | 0.350 | −0.25 | 0.00 | 0.00 | 0.01 |
| 0.0460 | 0.046 | 0.046 | 0.000 | 0.100 | −0.25 | 0.00 | 0.00 | 0.02 |
| 0.0460 | 0.023 | 0.020 | −0.08 | −0.605 | −0.25 | 0.00 | 0.00 | 0.01 |
| 0.0460 | 0.023 | 0.020 | 0.060 | −0.605 | −0.25 | 90.0 | 0.00 | 0.01 |
| 0.0560 | 0.040 | 0.100 | 0.060 | −0.105 | 0.625 | 90.0 | 0.00 | 0.02 |
| 0.0560 | 0.056 | 0.100 | 0.000 | −0.100 | 0.625 | 0.00 | 0.00 | −0.02 |
| 0.0230 | 0.023 | 0.023 | 0.000 | −0.605 | −0.25 | 0.00 | 0.00 | 0.01 |
| Cylinder Phantom with 11 Cylinders | | | | | | | | |
| 0.6900 | 0.6900 | 0.900 | 0.000 | 0.000 | 0.000 | 0.00 | 0.00 | 2.00 |
| 0.6624 | 0.6624 | 0.880 | 0.000 | 0.000 | 0.000 | 0.00 | 0.00 | −1.00 |
| 0.0800 | 0.0800 | 0.800 | 0.000 | 0.000 | 0.000 | 0.00 | 0.00 | 0.05 |
| 0.0800 | 0.0800 | 0.800 | 0.250 | 0.000 | 0.000 | 0.00 | 0.00 | 0.20 |
| 0.0800 | 0.0800 | 0.800 | 0.500 | 0.000 | 0.000 | 0.00 | 0.00 | −0.20 |

TABLE 2-continued

| a | b | c | $x_0$ | $y_0$ | $z_0$ | α | β | μ |
|---|---|---|---|---|---|---|---|---|
| 0.0800 | 0.0800 | 0.800 | −0.25 | 0.000 | 0.000 | 0.00 | 0.00 | 0.20 |
| 0.0800 | 0.0800 | 0.800 | −0.50 | 0.000 | 0.000 | 0.00 | 0.00 | −0.20 |
| 0.0800 | 0.0800 | 0.800 | 0.000 | 0.25 | 0.000 | 0.00 | 0.00 | 0.20 |
| 0.0800 | 0.0800 | 0.800 | 0.000 | 0.50 | 0.000 | 0.00 | 0.00 | −0.20 |
| 0.0800 | 0.0800 | 0.800 | 0.000 | −0.25 | 0.000 | 0.00 | 0.00 | 0.20 |
| 0.0800 | 0.0800 | 0.800 | 0.000 | −0.50 | 0.000 | 0.00 | 0.00 | −0.20 |

The total FACBR time contains the filtering time and backprojection time; the filtering time takes only a small part in the total time. After optimization of the filtering processing with SSE in PF data format, the timing result for 288 $512^2$ projections shown in Table 3 below is considered satisfactory, so it is not necessary to consider HE or HD optimization for filtering process.

TABLE 3

| Filter Mode | 4N_ext | SSE_4N | 2N_ext | SSE_2N |
|---|---|---|---|---|
| Time(s) | 146.891 | 58.163 | 78.753 | 35.310 |
| Speed-up | | 2.5255 | | 2.2303 |

The backprojection process is the most time-consuming part of FACBR. The acceleration of five implementations has been tested; the results are shown in Table 4 below. The tests used 288 $512^2$ projections to reconstruct $512^3$ data. All the reconstructions are run with a cylinder boundary. The program runs in Windows NT 4.0 and takes 95% to 98% of the processor time. The first column is the traditional PF method with boundary, the second is PF with data partition, the third one is HD method, the forth is HD data with HE, the fifth one is PF with SSE acceleration, and the last one is PF with HE. The results shows that HD provides a 3 to 3.5 speed-up over the traditional implementation, and HE-HD provides a 4 to 5 speed-up, which is almost same as PF with SSE. This result declares two points: first, the HE-HD does not involve the SSE unit, so that cheaper processor like the Celeron can be used to get almost the same performance with SSE-PF; second, a higher speed-up can be obtained by using a functional unit which works with fixed-point data in the same way in which the SSE works with floating-point data; such functionality already appears in the Pentium IV processor. The HE-PF is the most efficient method in a Pentium III processor. Reconstruction with sphere boundary, along with hybrid computing combining the power of the MMX and SSE units, provides a speed-up of 5 to 6 and a reconstruction time of 15.03 minutes for $512^3$ FACBR. The timing result will be better with a higher clock frequency processor and an SMP computer.

Table 5 below shows the effective $t_{unit}$ of different slices for the HE-HD and HE-PF methods. Since the program runs in a multi-processor operating system, the processor time resource varies over time, so that the effective $t_{unit}$ also varies over time. Basically, $t_{unit}$ becomes stable as the slice number increases. When the slice number is less than 4 or the data are not 16-bytes aligned, the processor is unable to use SSE, and then the $t_{unit}$ is greater than when SSE is available. Therefore, the time for a single slice can be greater than for other slices.

TABLE 5

| | | | Slice Number | | | |
|---|---|---|---|---|---|---|
| Method | | 1 | 32 | 64 | 128 | 256 | 512 |
| HE- | Time(s) | 4.126 | 68 | 148 | 308 | 671 | 1101 |
| PF | $t_{unit}$(ns) | 54.6 | 28.1 | 30.6 | 31.9 | 34.7 | 28.4 |
| HE- | Time | 5.033 | 76 | 166 | 348 | 681 | 1516 |
| HD | $t_{unit}$(ns) | 66.6 | 31.6 | 34.4 | 36.0 | 35.2 | 39.2 |

Precision will now be compared. The relative error between two images P and Q is calculated as $$E = \frac{1}{N_{pixel}} \sum \frac{|P_{i,j} - Q_{i,j}|}{\frac{1}{N_{pixel}} \sum |Q_{i,j}|} \times 100\% \qquad (5)$$

First, the error ratio will be calculated for each pixel. Then, the average error ratio will be calculated for the whole comparing Region of Interest (ROI).

Since HE-PF works with floating-point data, it will not introduce an extra precision error compared to tradition PF method. The greatest concern is whether HD computing will bring more precision error or not. If the relative precision error between a PF reconstructed image and a phantom image is $E_{PF}$, the relative error between a HD reconstructed image and a phantom image is $E_{HD}$, and the relative error between a HD reconstructed image and a PF reconstructed image is $E_{Hp}$, the ratio of the hybrid computing error to the whole precision error is defined as:

TABLE 4

| Slice and parameters | | Normal FD | PF | HD | HE-HD | SSE PF | HE-PF |
|---|---|---|---|---|---|---|---|
| 64 | Time(s) | 870 | 618 | 263 | 166 | 169 | 148 |
| | Speed-up | 1.0 | 1.408 | 3.308 | 5.241 | 5.148 | 5.878 |
| 128 | Time(s) | 1799 | 1256 | 529 | 348 | 349 | 308 |
| | Speed-up | 1.0 | 1.432 | 3.401 | 5.170 | 5.155 | 5.841 |
| 256 | Time(s) | 3288 | 2424 | 1040 | 681 | 744 | 671 |
| | Speed-up | 1.0 | 1.356 | 3.149 | 4.828 | 4.419 | 4.900 |
| 512 | Times | 6562 | 4714 | 2047 | 1516 | 1634 | 1101 |
| | Speed-up | 1.0 | 1.392 | 3.206 | 4.328 | 4.016 | 5.960 |

$$R_{HD} = \frac{|E_{HD} - E_{PF}|}{E_{HD}} \times 100\%. \qquad (6)$$

The precision error has been determined for a HD reconstructed image relative to a simulated phantom image and a PF reconstructed image. For the Shepp Logan phantom the precision error between the HD image and the PF image is less 0.03%; for the cylinder phantom, the $E_{HP}$ is less than 0.02%. Thus, the HD image keeps a good precision compared to the PF image. The $E_{HP}$ contributes less than 5% of the total error percentage to the simulated phantom image. This means that the algorithm introduces more than 95% of the total error. The HD images have enough precision and are comparable to PF images.

Figure 6:
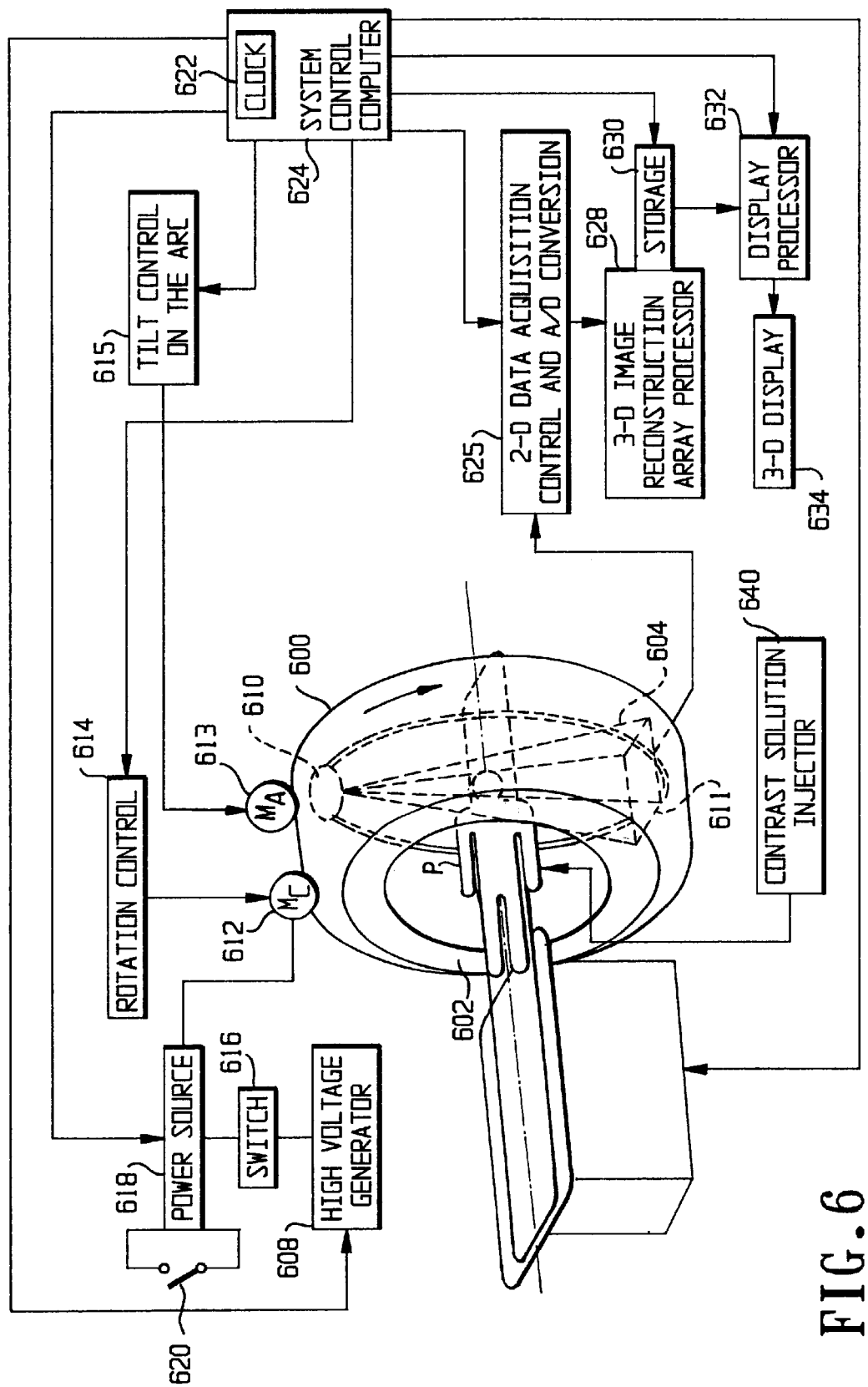
FIG. 6 shows a block diagram of a system on which the preferred embodiment of the present invention can be implemented.

An apparatus on which the invention can be implemented is shown in FIG. 6, which is reproduced from FIG. 9 of the above-referenced U.S. Pat. No. 5,999,587. In a standard CT, a 3-D reconstruction is obtained by stacking a series of slices. In a volume CT, a direct reconstruction of an object can be obtained. Referring now to FIG. 6, it is shown how the cone-beam tomography system 600 of the present invention can be used to obtain a direct 3-D reconstruction of an object. It should be understood that the cone beam volume CT scanning apparatus 600 is illustrated in a simplified block diagram form. The invention may preferably be employed in conjunction with such a cone beam volume CT scanning apparatus to generate a 3-D reconstruction matrix of the object. Based on the 3-D reconstruction matrix, the desired three-dimensional display can be obtained.

A cone beam volume CT scanning apparatus examines a body P using a cone shaped radiation beam 604 which traverses a set of paths across the body. As shown in FIG. 6, an x-ray source 610 and a 2-D detector 611 are mounted on a gantry frame 602 that rotates around the body P being examined. The operating voltage for the x-ray source is obtained from a conventional high-voltage generator 608 in such a manner that the x-ray source 610 produces the desired cone-shaped beam of radiation when the high-voltage is applied to it. The high-voltage generator 608 is energized by means of a power source 618, through a switch 616. A contrast solution injector 640 can be used as needed.

A first motor 612 is also powered by the power source 618 such that it drives the gantry frame 602 in its orbit about the body, for example, in a clockwise direction as shown by the arrows adjacent to the frame. The power source 618 is turned on by means of switch 620 or other conventional control devices, in order to initiate a measurement sequence. A speed control circuit 614 is used to control the speed of rotation of the gantry frame 602 and to provide an output control signal which indicates when the speed of the motor 712 is at the desired level for taking measurements. The output from the rotational control 614 may also be utilized to operate the switch 616 such that the high-voltage generator 608 is only turned on when the gantry frame 602 is driven at the desired speed for making measurements.

In order to obtain the arc measurements as previously discussed, a tilt control 615 is utilized to cause the gantry frame 602 to tilt by a relatively small angle of ±15° to ±30°, by means of the gantry frame tilt motor 613. That tilting allows the acquisition of arc projection data on the perpendicular arc. Such geometry results in a complete set of data for an object with a 25–40 cm diameter corresponding to a 37–60 cm field at the detectors 611 with a magnification of 1.5. Although the tilting of the gantry 602 is generally available in a standard CT gantry, to acquire arc projections, the minimal modification of a standard CT gantry has to be made such that the tilting of the gantry, the x-ray exposure timing and the projection acquisition are synchronized by the system control computer 624 as shown in FIG. 6.

In addition to the method above to acquire circle and arc projections, alternatively, the circle-plus-arc geometry can be implemented in one of the following two ways. In the first and preferred of the three methods, the gantry 602 is tilted to a small angle (±15° to ±30°) and then the x-ray tube 610 and the 2-D detector 611 are rotated while the gantry 602 is tilted. A half set of arc projections will be acquired only when the x-ray tube 610 and the 2-D detector 611 are at the rotation angle of 0°. When the tilted angle becomes zero, the circle projections will be acquired at the preset rotation angle positions. When the circle projection acquisition is completed, the gantry 602 will be tilted toward −15° to −30°. Another half set of arc projections will be acquired only when the x-ray tube 610 and the 2-D detector 611 are at the rotation angle of 0°.

The second alternative method is to mechanically modify a standard CT gantry such that two short arc orbits are added to the gantry, and the x-ray tube 610 and the 2-D detector 611 can be moved on the arc to acquire the arc projections and on the circle to acquire the circle projections. One arc constitutes the orbit of the x-ray tube 610 and the other arc is the orbit of the 2-D detector 611. The two arc orbits are mounted 180° apart from each other. The x-ray tube 610 and the 2-D detector 611 are synchronously moved on the arc orbits to acquire arc projections. Then, the x-ray tube 610 and the 2-D detector 611 are rotated on the gantry to acquire circle projections.

Mounted on the gantry frame 602 opposite the x-ray source 610 is a 2-D detector 611 which has a dynamic range equal to or greater than 1000:1 and an image lag of less than 10%, for example a selenium thin film transistor (STFT) array or a silicon STFT array, in order to provide 2-D projections that correspond to an x-ray attenuation signal pattern. The x-ray source 610 and the 2-D detector 611 are mounted on the gantry frame 602 in such a manner that they both move synchronously.

The cone-shaped beam of radiation 604 generated by the x-ray source 610 is projected through the body or object under test. The 2-D detector cone measures the radiation transmitted along the set of beam paths across the cone.

Alternatively, a continuous series of two-dimensional detectors (not shown) can be fixedly mounted proximate to the gantry frame 602 and the x-ray source 610 is mounted to the gantry frame such that, upon rotation of the gantry frame, the cone-shaped radiation beam 604 is projected through the body P under test and sequentially received by each of the series of detectors.

A 2-D projection acquisition control and A/D conversion unit 626, under control of the scanning pulses sequentially obtained from the system control computer 624, which includes the clock 622, receives a sequence of outputs corresponding to different lines of the 2-D detector 611. Each line of the 2-D detector consists of many detection cells (at least>100). The output of each detector cell represents a line integral of attenuation values measurable along one of the respective beam paths. The cone-shaped beam 604 subtends a cone angle sufficient to include the entire region of interest of the body. Thus, a complete scan of the object can be made by merely orbiting the gantry frame 602 supporting the x-ray source 610 and the 2-D detector 611 around the body to acquire the 2-D projection signals at different angular positions.

The analog-to-digital conversion unit 626 serves to digitize the projection signals and to save them in the 3-D image reconstruction array processor 628 and storage device 630. The method employed by the 3-D image reconstruction array processor 628 is the invented algorithm and method described in this application. The 3-D image reconstruction array processor 628 serves to transform the digitized projection signals into x-ray attenuation data vectors. The x-ray attenuation data matrix corresponds to x-ray attenuation at spaced grid locations within the body trunk being examined. Each data element of the matrix represents an x-ray attenuation value and the location of the element corresponds to a respective 3-D grid location within the body.

In accordance with the principles of the invention discussed previously, a display processor 632 obtains the data stored as 3-D x-ray attenuation signal patterns in the memory storage 630, processes that data as previously described, and then the desired 3-D images are displayed on a 3-D display device 634. The 3-D image reconstruction array processor 632 may, for example, be a computer as described above with one or more Intel or Intel-compatible x86-class microprocessors. However, any processor or processors capable of the same or substantially the same parallel operation can be used.

While a preferred embodiment of the present invention has been set forth above, those skilled in the art who have reviewed the present disclosure will readily appreciate that other embodiments can be realized within the scope of the present invention. For example, specific numerical values are illustrative rather than limiting, as are mentions of specific commercial products. The present invention is not specific to the Feldkamp algorithm, but can be used to implement any filtered backprojection cone-beam algorithms efficiently and optimally. Nor is the present invention specific to x86 processors; instead, the invention can be used with any processor capable of implementing the algorithms described above and has particular utility with any processor that has a floating-point unit that can process more than one single-precision 32-bit datum within one instruction set and a fixed-point unit that can process more than one 16- or 32-bit data within one instruction set. Therefore, the present invention should be construed as limited only by the appended claims.

What is claimed is:

1. A system for generating a three-dimensional image representative of an interior portion of an object, the system comprising:
    a radiation scanner which generates projection signals by passing a radiation through the object onto a detector; and
    a computer, receiving the projection signals, for generating the three-dimensional image by performing a plurality of calculations on the projection signals, the computer comprising at least one fixed-point processing unit and at least one floating-point processing unit, the at least one fixed-point processing unit operating in parallel with the at least one floating-point processing unit, the computer dividing the plurality of calculations into a first plurality of calculations to be performed in the at least one fixed-point processing unit and a second plurality of calculations to be performed in the at least one floating-point processing unit.

2. The system of claim 1, wherein the radiation scanner is a radiation cone-beam scanner, the radiation beam is a radiation come beam, and the projection signals are cone-beam projection signals.

3. The system of claim 2, wherein:
    the first plurality of calculations comprise generation of a projection map; and
    the second plurality of calculations comprise backprojection of the cone-beam projection signals in accordance with the projection map to produce the image.

4. The system of claim 3, wherein:
    the generation of the projection map comprises mapping a world coordinate system (x, y, z) to a coordinate system (u, t, s) of the detector, where u is independent of z;
    the computer organizes the cone-beam projection signals into z-lines for which varies but x and y are constant; and
    the computer performs the backprojection for each of the z-lines.

5. The system of claim 3, wherein, after the computer has performed the backprojection for all of the z-lines to form the image as a plurality of voxels, the computer performs a three-dimensional transpose operation on the voxels in the image to organize the voxels into x-lines for which x varies but y and z are constant.

6. The system of claim 4, wherein the computer further comprises a cache which is large enough to hold one of the z-lines.

7. The system of claim 1, wherein the projection signals are processed as pure floating-point data.

8. The system of claim 1, wherein the projection signals are processed as a mixture of floating-point and fixed-point data.

9. The system of claim 1, wherein the computer comprises a microprocessor on which the at least one fixed-point processing unit which can process more than one 16 bit or 32 bit integer data within one instruction set and the at least one floating-point processing unit which can process more than one single-precision 32 bit float point data within one instruction set are implemented.

10. The system of claim 9, wherein the computer comprises a plurality of said microprocessors, each of which comprises at least one said fixed-point processing unit which can process more than one 16 bit or 32 bit integer data within one instruction set and at least one said floating-point processing unit which can process more than one single-precision 32 bit float point data within one instruction set.

11. The system of claim 1, wherein the image is a linear attenuation coefficient distribution of the interior portion of the object.

12. The system of claim 1, wherein:
    a boundary of the object is known a priori; and
    the three-dimensional image is generated only within the boundary.

13. A method of generating a three-dimensional image representative of an interior portion of an object, the method comprising:
    (a) passing a through the object onto a detector to generate projection signals; and
    (b) receiving the projection signals and generating the three-dimensional image by performing a plurality of calculations on the projection signals;
        wherein step (b) is performed on a computer comprising at least one fixed-point processing unit and at least one floating-point processing unit, the at least one fixed-point processing unit operating in parallel with the at least one floating-point processing unit, the computer dividing the plurality of calculations into a first plurality of calculations to be performed in the at least one fixed-point processing unit and a second plurality of calculations to be performed in the at least one floating-point processing unit.

14. The method of claim 13, wherein the beam is a cone beam and the projection signals are cone-beam projection signals.

15. The method of claim 14, wherein:

the first plurality of calculations comprise generation of a projection map; and the second plurality of calculations comprise backprojection of the cone-beam projection signals in accordance with the projection map to produce the reconstructed image.

16. The method of claim 15, wherein:

the generation of the projection map comprises mapping a world coordinate system (x, y, z) to a coordinate system (u, t, s) of the detector, where u is independent of z;

the computer organizes the cone-beam projection signals into z-lines for which z varies but x and y are constant; and the computer performs the backprojection for each of the z-lines.

17. The method of claim 16, wherein the computer further comprises a cache which is large enough to hold one of the z-lines.

18. The method of claim 16, wherein, after the computer has performed the backprojection for all of the z-lines to form the image as a plurality of voxels, the computer performs a three-dimensional transpose operation on the voxels in the 19. The method of claim 14, wherein step (b) is performed using a filtered backprojection cone beam reconstruction algorithm.

20. The method of claim 19, wherein a filtered backprojection cone beam reconstruction algorithm is carried out using hybrid computing utilizing a single instruction multiple data technique.

21. The method of claim 20, wherein a filtered backprojection cone beam reconstruction algorithm is carried out using multi-threading over a plurality of processors. image to organize the voxels into x-lines for which x varies but y and z are constant.

22. The method of claim 14, wherein step (b) is performed through Feldkamp cone-beam reconstruction by:

(i) performing hybrid computing utilizing single instruction multiple data (SIMD) over a plurality of execution units;

(ii) using multi-thread and fiber support in an operating system so as to automatically enable reconstruction parallelism in a multi-processor environment effective datat I/O; and (iii) optimizing memory and cache access through data partitioning.

23. The method of claim 14, wherein step (b) is performed by parallel processing on a single microprocessor or multiple processors using hybrid computing to accelerate cone-beam reconstruction for reconstruction of soft tissue.

24. The method of claim 13, wherein the computer comprises a microprocessor on which the at least one fixed-point processing unit which can process more than one 16 bit or 32 bit integer data within one instruction set and the at least one floating-point processing unit which can process more than one single-precision 32 bit float point data within one instruction set are implemented.

25. The method of claim 24, wherein the computer comprises a plurality of the microprocessors, each of which comprises at least one said fixed-point processing unit which can process more than one 16 bit or 32 bit integer data within one instruction set and at least one said floating-point processing unit which can process more than 26. The method of claim 12, wherein the object comprises soft tissue.

27. The method of claim 26, wherein the image is used to detect cancer in the soft tissue.

28. The method of claim 12, wherein step (b) is performed using manually written assembly language. one single-precision 32 bit float point data within one instruction set.

29. The method of claim 13, wherein the image is a linear attenuation coefficient distribution of the interior portion of the object.

30. The method of claim 13, wherein the projection signals are processed as a mixture of floating-point and fixed-point data.

31. The method of claim 12, wherein step (b) is performed through multi-threading only when a plurality of processors are available.

32. The method of claim 13, wherein the projection signals are processed as pure floating-point data.

33. The method of claim 13, wherein:

a boundary of the object is known apriori; and the three-dimensional image is generated only within the boundary.

* * * * *